(12) United States Patent
Bourquin

(10) Patent No.: US 11,471,054 B2
(45) Date of Patent: Oct. 18, 2022

(54) LIGHT-BASED SKIN TREATMENT DEVICE

(71) Applicant: KONINKLIJKE PHILIPS N.V., Eindhoven (NL)

(72) Inventor: Yannyk Parulian Julian Bourquin, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 523 days.

(21) Appl. No.: 16/603,841

(22) PCT Filed: Apr. 9, 2018

(86) PCT No.: PCT/EP2018/058948
§ 371 (c)(1),
(2) Date: Oct. 9, 2019

(87) PCT Pub. No.: WO2018/189059
PCT Pub. Date: Oct. 18, 2018

(65) Prior Publication Data
US 2020/0113438 A1 Apr. 16, 2020

(30) Foreign Application Priority Data

Apr. 12, 2017 (EP) .................................... 17166245

(51) Int. Cl.
*A61B 5/00* (2006.01)
*A61N 5/06* (2006.01)

(52) U.S. Cl.
CPC .......... *A61B 5/0036* (2018.08); *A61B 5/0077* (2013.01); *A61B 5/441* (2013.01);
(Continued)

(58) Field of Classification Search
CPC ..... A61B 5/0036; A61B 5/0077; A61B 5/441; A61B 5/4848; A61B 2018/00452;
(Continued)

(56) References Cited

U.S. PATENT DOCUMENTS 3,174,414 A    3/1965 Myer
7,110,823 B2   9/2006 Vaynberg
(Continued)

FOREIGN PATENT DOCUMENTS

EP    1433430    6/2004
EP    2393040    12/2011

OTHER PUBLICATIONS

International Search Report and Written Opinion dated Jun. 13, 2018 for International Application No. PCT/EP2018/058948 Filed Apr. 9, 2018.

*Primary Examiner* — Jonathan T Kuo

(57) ABSTRACT

According to the invention, there is provided a light-based skin treatment device comprising a treatment light source; a treatment light exit window via which, during operation, treatment light generated by the treatment light source is applied to skin of a user, wherein the treatment light exit window comprises an optically transparent material arranged to contact the skin during operation; and an imaging unit comprising an image sensor 5 arranged to generate an image of the skin during operation. The skin treatment device further comprises an optical waveguide comprising a treatment light receiving surface, an imaging light exit surface and a main surface, wherein said treatment light receiving surface is arranged to receive the treatment light so that the treatment light enters the waveguide at the treatment light receiving surface; said main surface comprises the treatment light exit 10 window and is arranged to transmit the treatment light so that the treatment light exits the waveguide at the treatment light exit window; said imaging light exit surface is arranged with respect to the main surface to receive light reflected at the main surface by total internal reflection at positions where, during operation, no skin is in contact with the main surface; said image sensor is arranged to receive from the imaging light exit surface light which is (Continued)

15 guided by total internal reflection from the main surface towards the imaging light exit surface.

20 Claims, 10 Drawing Sheets

(52) U.S. Cl.
CPC .......... *A61B 5/4848* (2013.01); *A61N 5/0616* (2013.01); *A61N 2005/063* (2013.01); *A61N 2005/0628* (2013.01)

(58) Field of Classification Search
CPC ........ A61B 2018/0047; A61B 5/06–2005/073; A61N 5/0616; A61N 2005/0628; A61N 2005/063
See application file for complete search history.

(56) References Cited

U.S. PATENT DOCUMENTS

| | | |
|---|---|---|
| 9,687,298 B2 | 6/2017 | Mandre |
| 2005/0154382 A1* | 7/2005 | Altshuler ............. A61B 18/203 606/9 |
| 2007/0252997 A1 | 11/2007 | Van Hal |
| 2008/0147054 A1 | 6/2008 | Altshuler |
| 2013/0072803 A1 | 3/2013 | Altshuler |
| 2017/0156796 A1 | 6/2017 | Moeskops |

* cited by examiner (b)

(d)

(a)

(c)

LIGHT-BASED SKIN TREATMENT DEVICE

CROSS REFERENCE TO RELATED APPLICATIONS

This application is the U.S. National Phase application under 35 U.S.C. § 371 of International Application No. PCT/EP2018/058948 filed Apr. 9, 2018, published as WO 2018/189059 on Oct. 18, 2018, which claims the benefit of European Patent Application Number 17166245.5 filed Apr. 12, 2017. These applications are hereby incorporated by reference herein.

TECHNICAL FIELD OF THE INVENTION

The invention relates to a light-based skin treatment device, and in particular relates to a light-based skin treatment device having an image sensor for generating an image of skin of a user during operation.

BACKGROUND TO THE INVENTION

Skin treatment devices are known that use light to perform a treatment operation on the skin of a user. Such devices include intense pulsed light (IPL) devices, photo epilation devices, skin health assessment devices, skin rejuvenation devices, phototherapy devices or pain relief devices.

There is an increasing trend to provide connected or 'smart' products that have the ability to sense or monitor aspects of the treatment operation and adapt the treatment operation accordingly and/or to provide feedback to the user on the treatment operation. Thus, treatment solutions may become personalised and improve the primary treatment performance and experience.

In light-based skin treatment operations, it may be useful to obtain an image or images of the skin region being treated during operation, for example to observe or analyse the effect of the treatment operation on the skin region. As such, the treatment device may include a camera, or more generally an image sensor, for obtaining images of the skin region. However the presence of an image sensor in a treatment device creates privacy concerns for the user and other people around the user, since the image sensor could be used to obtain images of the environment when the treatment device is not being used on the skin.

US 2005/0154382 discloses a handheld dermatological device for visualizing a skin treatment region prior to, during, or after therapeutic treatment with therapeutic energy. In an embodiment the device comprises an optical guidance element in contact with the patient's skin during use and a light source able to illuminate the optical guidance element from a side surface thereof. A portion of the light entering the optical guidance element is refractively coupled into the skin at the interface of the optical guidance element and the skin and illuminates a subsurface region of the skin. This refractively coupled illumination light is scattered by the skin and focussed onto an image capture device to generate an image of the subsurface region of the skin. Furthermore, with respect to this embodiment, a total internal reflection mode is described wherein the illuminating light totally internally reflects from the skin contact surface of the optical guidance element. The total internal reflection mode is used for visualization of the skin surface.

There is therefore a need for an improved light-based skin treatment device that addresses or mitigates this problem.

SUMMARY OF THE INVENTION

According to the invention, there is provided a light-based skin treatment device comprising a treatment light source; a treatment light exit window via which, during operation, treatment light generated by the treatment light source is applied to skin of a user, wherein the treatment light exit window comprises an optically transparent material arranged to contact the skin during operation; and an imaging unit comprising an image sensor arranged to generate an image of the skin during operation; wherein the skin treatment device further comprises an optical waveguide comprising a treatment light receiving surface, an imaging light exit surface and a main surface; and wherein said treatment light receiving surface is arranged to receive the treatment light so that the treatment light enters the waveguide at the treatment light receiving surface; said main surface comprises the treatment light exit window and is arranged to transmit the treatment light so that the treatment light exits the waveguide at the treatment light exit window; said imaging light exit surface is arranged with respect to the main surface to receive light reflected at the main surface by total internal reflection at positions where, during operation, no skin is in contact with the main surface; said image sensor is arranged to receive from the imaging light exit surface light which is guided by total internal reflection from the main surface towards the imaging light exit surface. Thus, the invention provides that an image can be obtained of the skin region that is being treated, while preventing the image sensor from obtaining an image of the environment outside the optical waveguide when there is no skin in contact with the optical waveguide, which reduces privacy concerns for users of the skin treatment device.

In an embodiment of the skin treatment device according to the invention, the image sensor is arranged to generate the image based on parts of the light reflected at the main surface by total internal reflection at positions that are not in contact with skin during operation and attenuated light caused by frustrated total internal reflection of light at positions on the main surface in contact with skin during operation.

In a further embodiment of the skin treatment device according to the invention, the optical waveguide further comprises an imaging light reflecting surface different from the main surface for reflecting at least part of the treatment light received by the treatment light receiving surface towards the main surface such that said reflected part of the treatment light is reflected towards the imaging light exit surface at the main surface by total internal reflection at positions where, during operation, no skin is in contact with the main surface. This embodiment has the advantage that no additional light source is required for illuminating the skin in order to obtain the image.

In this embodiment, the treatment light source and the imaging light reflecting surface may be arranged with respect to the optical waveguide such that said part of the treatment light reflected from the imaging light reflecting surface is incident on the main surface at an angle less than a critical angle measured with respect to the main surface for the optical waveguide. Preferably, in this embodiment the treatment light source and the imaging light reflecting surface are arranged with respect to the optical waveguide such that said part of the treatment light reflected from the imaging light reflecting surface is incident on the main surface at an angle in a range of 4° to 50° with respect to the main surface, or in a range of 10° to 35° with respect to the main surface, or in a range of 13° to 30° with respect to the main surface.

In an alternative embodiment of the skin treatment device according to the invention, the imaging unit further comprises an imaging light source different from the treatment light source, the optical waveguide further comprises an imaging light receiving surface different from the treatment light receiving surface for receiving imaging light generated by the imaging light source, and the imaging light receiving surface is arranged with respect to the main surface such that imaging light received by the imaging light receiving surface is incident on the main surface and reflected towards the imaging light exit surface by total internal reflection at positions where, during operation, no skin is in contact with the main surface.

In this embodiment, the imaging light source may be arranged with respect to the optical waveguide such that the imaging light is incident on the main surface at an angle less than a critical angle measured with respect to the main surface for the optical waveguide.

In this embodiment, preferably the imaging light source is arranged with respect to the optical waveguide such that the imaging light is incident on the main surface at an angle in a range of 4° to 50° with respect to the main surface, or in a range of 10° to 35° with respect to the main surface, or in a range of 13° to 30° with respect to the main surface.

In some embodiments, the refractive index of the optical waveguide is the same as or similar to the refractive index of skin.

In a particular embodiment of the skin treatment device according to the invention, the skin treatment device further comprises a processing unit that is configured to receive the image from the image sensor and to process the received image.

In this embodiment, the processing unit may be configured to process the received image to determine a location of the light-based skin treatment device on the skin of the user, determine an effect of the treatment light on the skin being treated, and/or determine an operating parameter or a change in operating parameter for the treatment light source.

In this embodiment, the processing unit may be configured to process the received image to identify features of the skin in contact with the treatment light exit window, and to determine the location of the light-based skin treatment device on the skin of the user based on the identified features of the skin.

In this embodiment, the processing unit may be configured to process the received image to identify features of the skin in contact with the treatment light exit window, and to determine the location of the light-based skin treatment device on the skin of the user by comparing the identified features of the skin to one or more reference images associated with different locations on the skin.

In this embodiment, the processing unit may be configured to process the received image to identify features of the skin in contact with the treatment light exit window, and to determine the location of the light-based skin treatment device on the skin by comparing the identified features of the skin to information on the features of the skin for different parts of the skin that is stored in a database.

In these embodiments, the identified features of the skin may comprise any one or more of contours or surface texture features of the skin such as fine lines and pores, distance between contours or surface texture features of the skin, the colour of the skin, the composition of the skin, the presence of hairs, the density of hairs, the thickness of hairs and the colour of hairs.

In a preferred embodiment of the skin treatment device according to the invention, the skin treatment device further comprises a pressure sensor for measuring a pressure with which the treatment light exit window is pressed onto the skin of the user, wherein the processing unit is configured to process the measured pressure to determine an amount of distortion present in the received image due to the pressure.

In a further embodiment of the skin treatment device according to the invention, the processing unit is further configured to process the received image to estimate an amount of distortion in the image due to a pressure with which the treatment light exit window is pressed on to the skin of the user, and to estimate the pressure with which the treatment light exit window is pressed on to the skin of the user based on the estimated distortion.

In a yet further embodiment of the skin treatment device according to the invention, the processing unit is further configured to process the received image to compensate for noise in the image due to contaminants on the treatment light exit window. In this embodiment, the processing unit may be configured to compensate for noise in the received image using a reference image obtained when the treatment light exit window was not in contact with the body of the user.

In a further embodiment of the skin treatment device according to the invention, the processing unit is further configured to process the received image to determine an amount of contaminants on the treatment light exit window, and to issue an alert to the user if the amount of contaminants is above a threshold amount.

In a preferred embodiment of the skin treatment device according to the invention, the skin treatment device is an intense pulsed light (IPL) device, a photo epilation device, a light-based skin health assessment device, a light-based skin rejuvenation device, a phototherapy device or a light-based pain relief device.

BRIEF DESCRIPTION OF THE DRAWINGS

For a better understanding of the invention, and to show more clearly how it may be carried into effect, reference will now be made, by way of example only, to the accompanying drawings, in which.

DETAILED DESCRIPTION OF THE PREFERRED EMBODIMENTS

Figure 1:
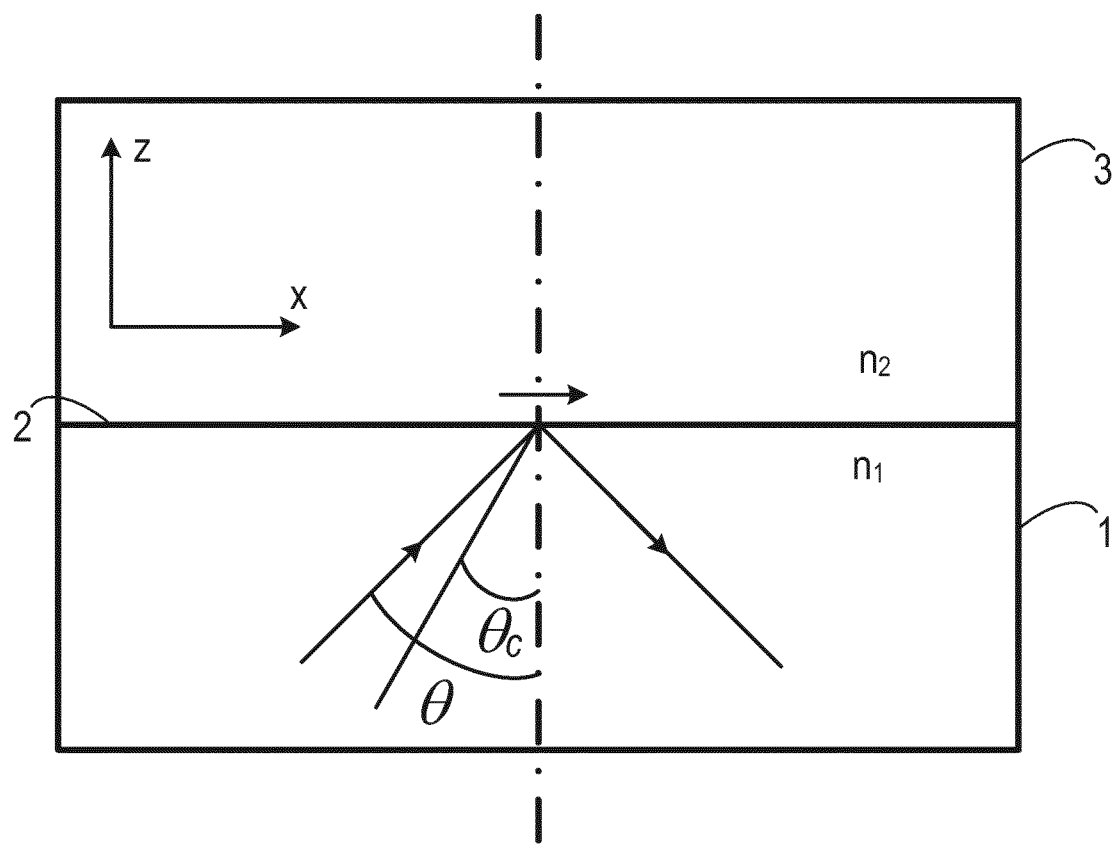
FIG. 1 is an illustration of the principle of total internal reflection of light.

As noted above, in light-based skin treatment operations it may be useful to obtain an image or images of the skin region being treated during the treatment operation. These images can be used for a number of purposes, some of which are described in more detail below. Thus, the skin treatment device may include an image sensor for obtaining images of the skin, and particularly of the skin region being treated.

However the presence of an image sensor in a skin treatment device creates privacy concerns for the user and other people around the user since the image sensor could be used to obtain images of the environment (and thus the people in the environment) when the skin treatment device is not being used on the skin. The present invention addresses this problem by providing an arrangement of the image sensor (and more particularly an imaging unit that comprises the image sensor) and an optical waveguide that allows images to be obtained of a skin region being treated, but prevents images being obtained of the environment around the skin treatment device when a skin region is not being treated.

The invention makes use of the well-known principle of total internal reflection of light, which is briefly described below with reference to FIG. 1. Total internal reflection (TIR) is a phenomenon that occurs when a light wave propagating in a first medium 1 (e.g. glass) strikes a boundary 2 between the first medium 1 and a second medium 3 (e.g. air) having a lower refractive index than the first medium 1 at an angle larger than a critical angle $\theta_c$ (measured with respect to an axis extending perpendicularly from the boundary 2). In this case, all the light waves are reflected at the boundary 2. The critical angle $\theta_c$ is defined by:

$$\theta_c = \arcsin(n_2/n_1) \quad (1)$$

where $n_1$ is the refractive index of the first medium 1 and $n_2$ is the refractive index of the less dense (second) medium 3.

When TIR occurs, an evanescent wave (also known as an evanescent field) is present adjacent the boundary 2 in the less dense (second) medium 3 as shown in FIG. 1. The intensity I of the evanescent wave decays exponentially from the boundary 2 into the lower refractive index medium 3 according to $$I(z) = I(0)\exp(-z/d) \quad (2)$$

where I(0) is the intensity at the boundary 2, z is the perpendicular distance from the boundary 2 and d is the depth of penetration of the evanescent wave into the second medium 3, defined as the distance over which the intensity of the evanescent field decays to 1/e of its value at the boundary 2.

Under ordinary conditions (i.e. where the boundary 2 is formed by the two mediums 1, 3, the evanescent wave transmits zero net energy across the boundary 2. However, if a third medium with a higher refractive index than the lower refractive index second medium 3 is placed a distance of less than several wavelengths from the interface 2 between the first medium 1 and the second medium 3, the evanescent wave will be different, and energy will pass across the second medium 3 into the third medium. This process is called "frustrated" total internal reflection (FTIR).

Figure 2:
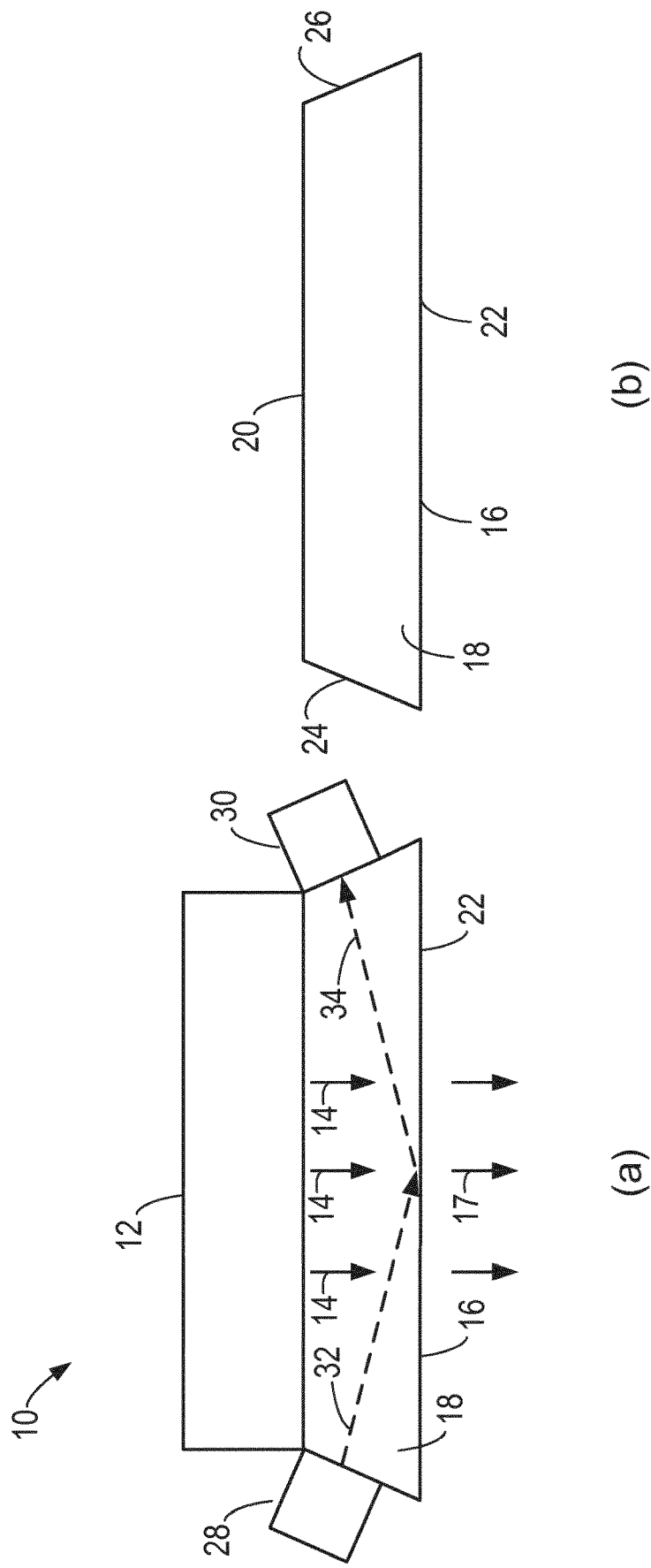
FIG. 2 is a cross-section through an exemplary skin treatment device according to a first embodiment of the invention.

FIG. 2 illustrates an exemplary first embodiment of a skin treatment device according to the invention. In particular, FIG. 2(a) shows a cross-section through part of an exemplary skin treatment device, and FIG. 2(b) shows a component of the skin treatment device in isolation for ease of understanding.

The skin treatment device 10 in FIG. 2(a) comprises a treatment light source 12 for generating light to perform a treatment operation of the skin of a user. In this respect, the term "treatment operation" has to be interpreted as any substantial treatment of the skin, other than merely illuminating the skin for imaging purposes, such as hair-growth reduction or hair removal treatments, skin rejuvenation treatments, wrinkle reduction treatments, or any other light-based skin treatment known to the skilled person and providing a substantial treatment effect to the skin. The treatment light source 12 can generate any suitable type of light for performing a treatment operation, e.g. light at any suitable or desired wavelength(s) and/or intensities. For example the treatment light source 12 can generate visible light, infra-red (IR) light and/or ultraviolet (UV) light. The treatment light source 12 can comprise any suitable type of light source, such as one or more light emitting diodes (LEDs), a gas-discharge or flash lamp, a laser or lasers, etc. Light generated by the treatment light source 12, indicated generally by arrows 14 and referred to as 'treatment light', is emitted by the treatment light source 12 and towards a treatment light exit window 16. When the skin treatment device 10 is being used to apply or perform a light-based treatment on the skin of a user, the skin treatment device 10 is positioned such that the treatment light exit window 16 is adjacent to or on the skin region to be treated so that treatment light from the treatment light source 12 illuminates the skin region.

The treatment light source 12 is arranged with respect to the treatment light exit window 16 such that at least some of the generated treatment light 14 passes through the treatment light exit window 16 and into or onto the skin region to be treated. The treatment light that passes through the treatment light exit window 16 is labelled 17 in FIG. 2(a).

That is, the treatment light source 12 is arranged with respect to the treatment light exit window 16 such that total internal reflection of the treatment light does not occur at the treatment light exit window 16. The treatment light exit window 16 comprises a partially or fully optically transparent material (e.g. glass, plastic, fused silica, borosilicate (BK7), sapphire, ceramic, polymers). That is, the treatment light exit window 16 can comprise or be formed from a material that is transparent to at least one wavelength of visible, IR or UV light.

In addition to the treatment light source 12, the skin treatment device 10 comprises an optical waveguide 18 that is provided adjacent the treatment light source 12. The treatment light source 12 emits the treatment light into the optical waveguide 18.

The optical waveguide 18 is shown in isolation in FIG. 2(b). In this embodiment, the optical waveguide 18 comprises a treatment light receiving surface 20, a main surface 22 that is on the opposite side of the optical waveguide 18 to the treatment light receiving surface 20, an imaging light receiving surface 24 and an imaging light exit surface 26. The main surface 22 provides the boundary between the optical waveguide 18 and the air and/or skin of the user. The imaging light receiving surface 24 and imaging light exit surface 26 are oriented and positioned on the optical waveguide 18 such that light entering the imaging light receiving surface 24 at at least one angle can be totally internally reflected by the main surface 22 towards the imaging light exit surface 26. Those skilled in the art will be aware of various geometries and configurations of the optical waveguide 18 that can enable this functionality.

The optical waveguide 18 is provided to space the treatment light source 12 from the skin of the user and allow an image of the skin region being treated to be obtained. The optical waveguide 18 may also improve the coupling of the treatment light from the treatment light source 12 to or into the skin.

The treatment light receiving surface 20 receives the treatment light from the treatment light source 12, so that the treatment light enters the optical waveguide 18 at the treatment light receiving surface 20 and propagates towards the main surface 22 of the optical waveguide 18. The main surface 22 provides the exit surface for the treatment light and thus the main surface 22 comprises (e.g. includes, is or forms) the treatment light exit window 16. The treatment light receiving surface 20 and main surface 22 are arranged (i.e. oriented) with respect to each other so that at least some of the treatment light can pass through the optical waveguide 18 and out of the main surface 22 into or onto the skin region to be treated. For example, the treatment light receiving surface 20 and main surface 22 can be parallel or substantially parallel to each other. The optical waveguide 18 can comprise or be formed from a material that is transparent to at least one wavelength of visible, IR or UV light (e.g. glass or plastic). The refractive index of the optical waveguide 18 can be selected to match the refractive index of skin. The refractive index of skin (particularly the epidermis) is typically between 1.42 and 1.48, depending on the wavelength of the incident light. In preferred embodiments, the refractive index of the optical waveguide 18 is preferably equal to or higher than the refractive index of the skin. However, in other embodiments, the refractive index of the optical waveguide 18 can be lower than the refractive index of the skin.

In order to obtain an image or series of images of the skin region being treated during a treatment operation, the skin treatment device 10 comprises an imaging unit 27 for generating the image or images. Since the skin treatment device 10 can be pressed into contact with the skin of the user during operation (which for example has the benefit that the treatment light only illuminates the desired area and does not impinge on, for example, the user's eye(s)), additional light is required to enable the imaging unit 27 to generate the images. In this exemplary embodiment, this additional light is provided by a light source separate from the treatment light source 12.

Thus, the imaging unit 27 comprises an imaging light source 28 and an image sensor 30, with the imaging light source 28 generating light for enabling the image sensor 30 to generate an image of the skin. The imaging light source 28 can generate any suitable type of light for forming the image, for example the imaging light source 28 can generate visible light, IR light and/or UV light. In some embodiments, the light generated by the imaging light source 28 is white light. In some embodiments, the imaging light source 28 is a light emitting diode (LED) or laser-based light source. Light generated by the imaging light source 28 is referred to herein as 'imaging light', and is thus distinct from the treatment light generated by the treatment light source 12. It will be appreciated that the imaging light can be a different wavelength to the treatment light. Using imaging light that has a different wavelength to the treatment light can enable the image sensor 30 to form the image from only the imaging light (e.g. by using a suitable filter to prevent the treatment light reaching the image sensor 30). Alternatively, the imaging light source 28 and treatment light source 12 can be activated at different times so that the image sensor 30 obtains or generates an image when the skin is not being illuminated by the treatment light. This can improve the quality of the obtained image.

The imaging light source 28 is arranged with respect to the optical waveguide 18 such that the imaging light source 28 emits imaging light towards the imaging light receiving surface 24 on the optical waveguide 18 and, on entering the optical waveguide 18, the imaging light propagates towards the main surface 22 of the optical waveguide 18. In particular, the imaging light, indicated generally by arrow 32 in FIG. 2(a), propagates towards the treatment light exit window 16.

It will be appreciated that, although FIG. 2(a) shows the imaging light source 28 in contact with the imaging light receiving surface 24, other arrangements are possible, for example the imaging light source 28 can be spaced from the imaging light receiving surface 24, e.g. with the light from the imaging light source 28 being directed towards the imaging light receiving surface 24 via one or more mirrors or other optical elements.

The imaging light source 28 is oriented with respect to the main surface 22 such that the imaging light 32 is incident on the main surface 22 at an angle greater than the critical angle $\theta_c$ for the optical waveguide 18 and air (where the critical angle is measured from an axis extending perpendicularly from the main surface 22), which means that, when no skin (or other object having a higher refractive index than air) is in contact with the main surface 22, total internal reflection of the imaging light 32 occurs at the main surface 22. The imaging light that is totally internally reflected at the main surface 22 is indicated by arrow 34.

The image sensor 30 is arranged with respect to the optical waveguide 18 such that the image sensor 30 receives the imaging light 34 that has been totally internally reflected by the main surface 22 towards the imaging light exit surface 26. Thus, the imaging light exit surface 26 and the image sensor 30 are oriented with respect to the main surface 22 at the same or a similar angle to the angle of the imaging light receiving surface 24 and the imaging light source 28 with respect to the main surface 22. In other words, the image sensor 30 is positioned at an angle greater than the critical angle $\theta_c$ for the optical waveguide 18 and air. The image sensor 30 can be arranged in contact with or adjacent to the imaging light exit surface 26 such that light exiting the optical waveguide 18 at the imaging light exit surface 26 is received by the image sensor 30.

The image sensor 30 can be any suitable type of sensor for forming an image from received light. The image can be a digital image that comprises a plurality pixels, for example several thousand or several million pixels, depending on the resolution required for the obtained images. The image sensor 30 can be, for example, a charge-coupled device (CCD)-based sensor, or a complementary metal-oxide-semiconductor (CMOS)-based image sensor. Those skilled in the art will be aware of other types of sensors that can be used.

This arrangement of imaging unit 27 enables an image to be obtained of the skin region that is in contact with or adjacent to the treatment light exit window 16, and thus enables an image to be obtained of the skin region actually being treated.

Moreover, due to the angle of the image sensor 30 with respect to the main surface 22, and the total internal reflection of the imaging light 32 by the main surface 22 when there is no skin in contact with the treatment light exit window 16, the image sensor 30 is unable to obtain an image of the environment outside the optical waveguide 18 when there is no skin in contact with the optical waveguide 18, which reduces privacy concerns for users of the skin treatment device 10.

Although not shown in FIG. 2(*a*), to further improve the image generation and/or privacy control provided by the arrangement shown in FIG. 2(*a*), the imaging unit 27, and in particular the image sensor 30, may comprise one or more components for focussing the image sensor 30 at the treatment light exit window 16 so that the possibility of light from the environment reaching the image sensor 30 is further reduced. For example, the image sensor 30 can be provided with a lens or lens arrangement to focus the image sensor 30 at the treatment light exit window 16. Alternatively or in addition, the numerical aperture (NA) of the image sensor 30 can be selected so that the image sensor 30 cannot receive light from the environment that enters the optical waveguide 18 via the treatment light exit window 16 and the main surface 22. This is described in more detail below with reference to FIG. 4.

Figure 3:
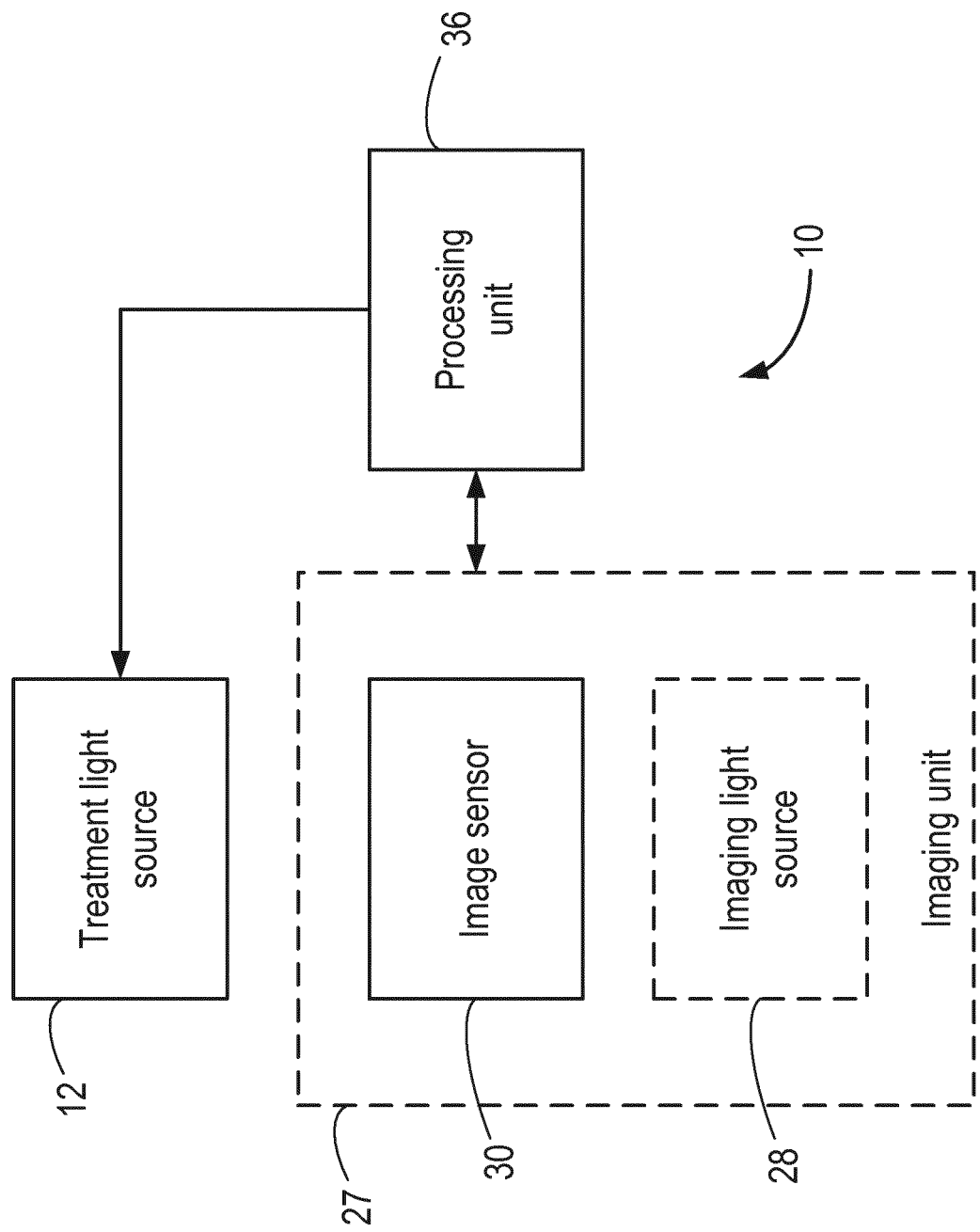
FIG. 3 is a block diagram showing various components of a skin treatment device according to an embodiment of the invention.

FIG. 3 is a block diagram showing various components of a skin treatment device 10 according to an embodiment. In particular FIG. 3 shows the treatment light source 12 and imaging unit 27 connected to a processing unit 36. The processing unit 36 generally controls the operation of the skin treatment device 10. For example the processing unit 36 can control the activation, deactivation and/or operation of the treatment light source 12 to start, stop or adjust a light-based skin treatment. In addition, the processing unit 36 can control the activation of the imaging unit 27 and the capture of images by the image sensor 30. In further embodiments, which are described in more detail below, the processing unit 36 can process or analyse the images obtained by the image sensor 30 to determine the location of the skin treatment device 10 on the skin of the user, an effect of the skin treatment on the skin region being treated and/or to determine an operating parameter or a change in operating parameter for the light-based treatment operation.

The processing unit 36 can be implemented in numerous ways, with software and/or hardware, to perform the various functions described below. The processing unit 36 may comprise one or more microprocessors or digital signal processors (DSPs) that may be programmed using software or computer program code to perform the required functions and/or to control components of the processing unit 36 to effect the required functions. The processing unit 36 may be implemented as a combination of dedicated hardware to perform some functions (e.g. amplifiers, pre-amplifiers, analogue-to-digital convertors (ADCs) and/or digital-to-analogue convertors (DACs)) and a processor (e.g., one or more programmed microprocessors, controllers, DSPs and associated circuitry) to perform other functions. Examples of components that may be employed in various embodiments of the present disclosure include, but are not limited to, conventional microprocessors, DSPs, application specific integrated circuits (ASICs), and field-programmable gate arrays (FPGAs).

The processing unit 36 can comprise or be associated with a memory unit, such as a volatile or non-volatile computer memory such as RAM, PROM, EPROM, and EEPROM. The memory unit can be used for storing program code that can be executed by a processor in the processing unit 36 to cause the skin treatment device 10 to perform the various functions described herein.

It will be appreciated that FIGS. 2 and 3 only show part of a skin treatment device 10 according to an embodiment of the invention, and thus a skin treatment device 10 will typically include additional components to those shown. For example, the skin treatment device 10 can comprise a housing portion for housing the treatment light source 12, optical waveguide 18 and imaging unit 22. The housing portion may be formed into a handle or other configuration that enables a user to hold and use the skin treatment device 10 to perform the skin treatment operation. The skin treatment device 10 may also comprise a power source, e.g. a battery, or components for connecting the skin treatment device 10 to a mains power supply. The skin treatment device 10 may also or alternatively include one or more user interface components, such as buttons, switches, screens, lights, speakers, etc. for receiving inputs from the user of the skin treatment device 10 (e.g. to activate and deactivate the light treatment) and/or to provide information to the user, such as the obtained image(s) or information derived using the obtained images.

Figure 4:
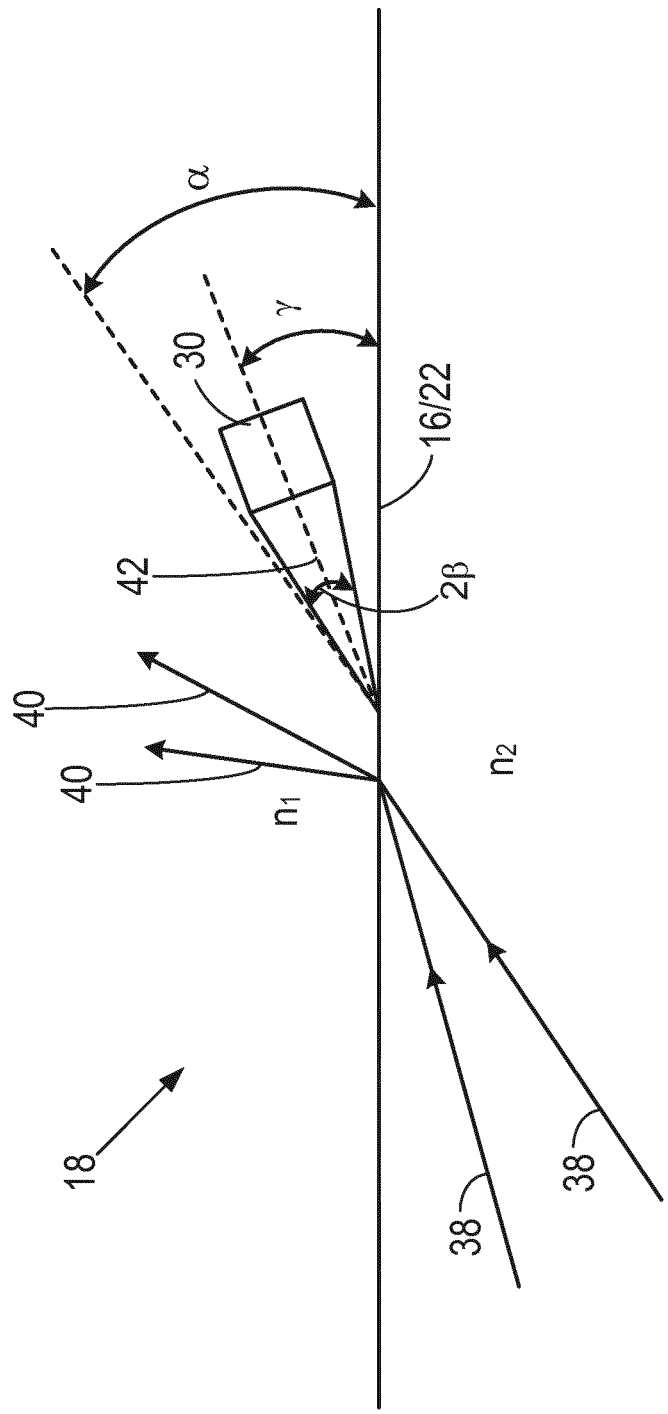
FIG. 4 is an illustration of an exemplary arrangement of an image sensor with respect to an optical waveguide in a skin treatment device according to the invention.

Thus, as noted above, due to the angle of the image sensor 30 with respect to the main surface 22 and the treatment light exit window 16, imaging from outside of the optical waveguide 18 by the image sensor 30 is not possible, preventing any privacy issue. FIG. 4 shows an exemplary arrangement of the image sensor 30 with respect to the optical waveguide 18. The optical waveguide 18 is shown as having a refractive index $n_1$, and the air has a refractive index $n_2$, where $n_1 > n_2$. Light coming from the environment, labelled with arrow 38, that is generally incident towards the image sensor 30 will be refracted at the main surface 22 and the treatment light exit window 16 into the optical waveguide 18 such that it is not detectable by the image sensor 30, as shown by refracted light 40.

This effect is due to the position of the image sensor 30 with respect to the main surface 22 (shown as an angle $\gamma$ measured with reference to the main surface 22, which can also be understood as the angle of the lens associated with the image sensor 30), where $\gamma < (90 - \theta_c)$. The angle $\alpha$ represents the maximum angle of the light reflected from the main surface 22 that the image sensor 30 (and associated lens) is able to capture. In addition, the numerical aperture (NA) of the image sensor 30, indicated by region 42 in FIG. 4, means that the image sensor 30 is not sensitive to light from outside this region 42. For a numerical aperture defined by:

$$NA = n_1 \cdot (\sin \beta) \quad (3)$$

where $\beta$ is the half-angle of the cone of region 42. $\beta$ should be less than $\alpha/2$. In addition, angle $\gamma$ should not be larger than $\alpha - \beta$.

Those skilled in the art will be able to determine a suitable value for the angle $\gamma$, but as an example, consider the optical waveguide 18 being formed from a material having a refractive index $n_1 = 1.4$ and a vacuum having a refractive index $n_2 = 1$. In this case, the image sensor 30 can be placed to detect totally internally reflected light 34 with an angle $\gamma$ below 45° with respect to the main surface 22. The lens/image sensor 30 can be placed, for example, at an angle of 22° with respect to the plane of the main surface 22, and with a numerical aperture of 0.52 corresponding to a half angle of the cone 42 ($\beta$) of 22.2°. In this configuration, no external light 38 (i.e. light from outside the optical waveguide 18 incident on the main surface 22) can propagate at an angle below 45° in the optical waveguide 18.

Thus, the optimal angle of the imaging light source 28 and the image sensor 30 depends on the refractive index of the material used for the optical waveguide 18. In the case of an optical waveguide 18 formed from glass with a refractive index of 1.4, an angle γ for the image sensor 30 with respect to the main surface 22 can be in a range of 10° to 35°, or in a range of 13° and 30°. In the case of an optical waveguide 18 formed from sapphire with a refractive index of 1.77, an angle γ for the image sensor 30 with respect to the main surface 22 can be in a range of 14° to 40°, preferably around 27°. It will be appreciated that the imaging light source 28 can be arranged at a similar angle γ with respect to the main surface 22 such that the imaging light 32 is incident on to the main surface 22 at an angle in a range of 4° to 50° with respect to the main surface 22, an angle in a range of 10° to 35° with respect to the main surface 22 or an angle in a range of 13° to 30° with respect to the main surface 22.

Figure 5:
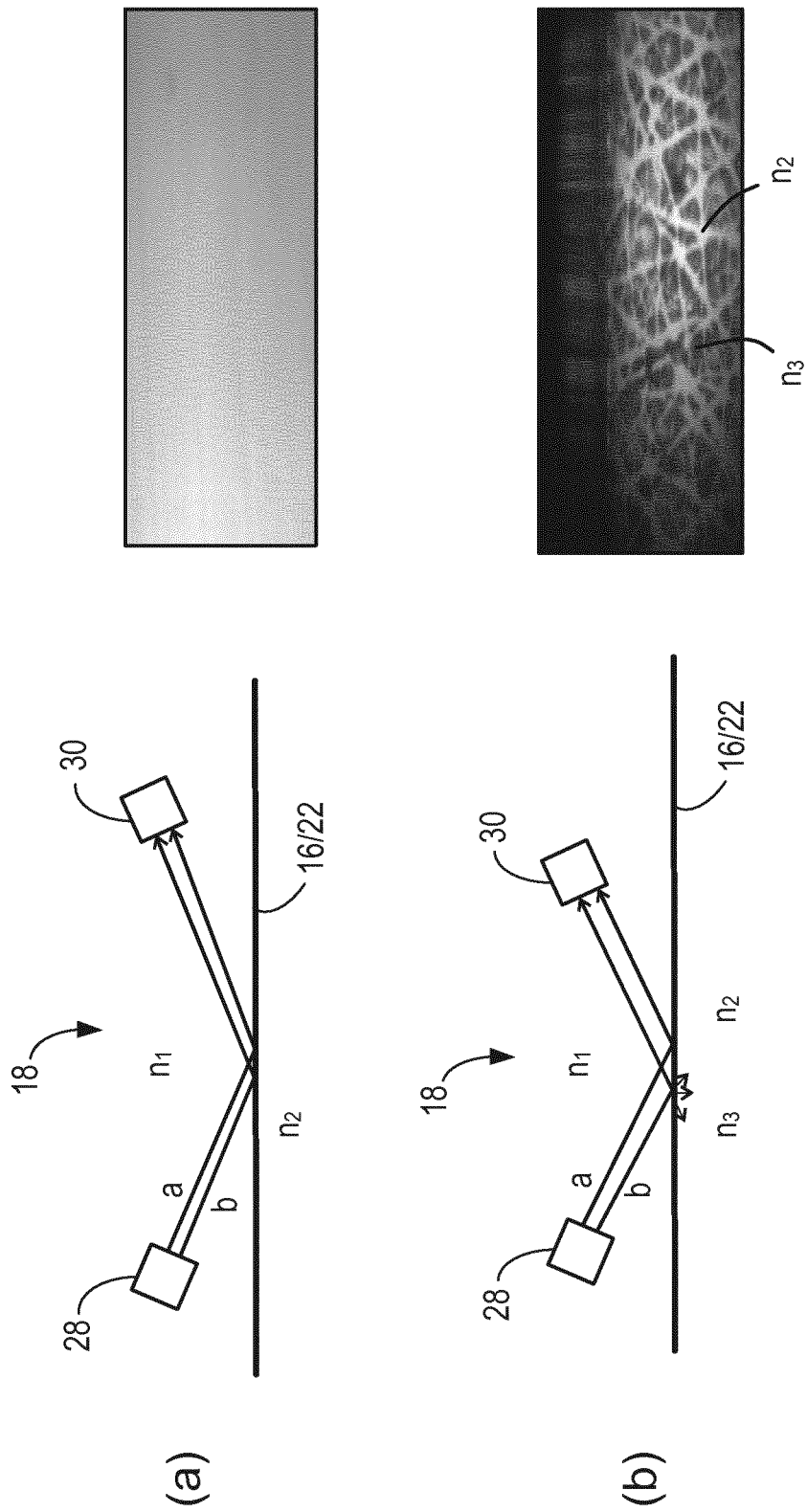
FIG. 5 shows the images obtained by an image sensor when nothing is in contact with the treatment light exit window and when skin is in contact with the treatment light exit window.

As noted above with reference to FIG. 1, the total internal reflection of the imaging light 32 at the main surface 22 creates an evanescent field on the other side of the main surface 22. When no skin (or other object, such as hair) having a higher refractive index than air) is in contact with the optical waveguide 18, the evanescent field does not transmit any energy across the main surface 22 into the air. FIG. 5(*a*) shows an image obtained by the image sensor 30 when there is nothing in contact with the optical waveguide 18 other than air. In particular FIG. 5(*a*) shows two spatially separate light beams a and b emitted by the imaging light source 28 that are incident on to the main surface 22. Air is in contact with the optical waveguide 18 (but nothing else), and so total internal reflection of the light beams a and b occurs at the main surface 22 towards to the image sensor 30. The image sensor 30 therefore receives all light from the imaging light source 28 and the obtained image is a homogenous bright surface, as shown in FIG. 5(*a*).

It will be appreciated that the image shown in FIG. 5(*a*) demonstrates the privacy benefits of the arrangement in FIG. 2. In particular, if the imaging unit 27 is active when the optical waveguide 18 is not in contact with the skin, for example when placed down by the user between treatment operations and/or angled during the operation so that the image sensor 30 and/or the treatment light exit window 16 faces the environment rather than the body, the image sensor 30 will only be able to obtain a homogenous bright image due to the reflection of the imaging light from the imaging light source 28, preventing any image being obtained of the environment.

However, when a part of the skin of the user is in contact with the main surface 22 and treatment light exit window 16, for example when a treatment operation is being performed, the part of the skin that gets into contact with the treatment light exit window 16 will scatter the light in the evanescent field. It will be appreciated that the skin does not have a uniformly flat surface, as there are undulations, folds, fine lines, pores, wrinkles, creases, hairs, etc., which means that, when a part of the skin is in contact with the treatment light exit window 16, some parts of the skin will be in close or actual contact with the treatment light exit window 18 (e.g. within a few nanometres, nm) and, due to the undulations, folds, fine lines, pores, wrinkles, creases, etc., there will be other parts of the skin that are not in contact with the treatment light exit window 18. At the locations of these other parts of the skin not in contact with the treatment light exit window 18, there will be an air gap between the skin and the treatment light exit window 16. At locations where said close or actual contact occurs between the skin and the treatment light exit window 16, the energy in the evanescent field at that locations will be scattered. At locations where an air gap is present, total internal reflection of the incident imaging light will still occur.

FIG. 5(*b*) shows an image obtained by the image sensor 30 when a part of the skin is in contact with the treatment light exit window 16, for example during a light-based treatment operation. In particular FIG. 5(*b*) shows two spatially separate light beams a and b emitted by the imaging light source 28 that are incident on to the main surface 22. Light beam a is incident on a part of the main surface 22 that is not in contact with skin (e.g. due to an air gap formed by a crease or fold in the skin), and so light beam a is totally internally reflected at the main surface 22 towards the image sensor 30. This light beam a will produce a bright pixel at the image sensor 30 (with suitable focusing of the incident light). However, light beam b is incident on a part of the main surface 22 that is in contact with skin (with refractive index $n_3$), and so the skin scatters light from the evanescent field at that point (due to frustrated total internal reflection), reducing or attenuating the intensity of the reflection of light beam b at the main surface 22 towards the image sensor 30. This produces a pixel at the image sensor 30 that has a lower brightness (i.e. darker) than that produced by totally-internally-reflected light beam a, with the brightness of the pixel dependent on how much light has been scattered by the evanescent field. The amount of scattering (and thus the brightness of the pixel at the image sensor 30) can depend on the optical properties of the skin at that location, e.g. stratum corneum, sebum, hairs, etc. The combination of the bright pixels resulting from totally internally reflected light and less bright pixels resulting from light that has been partly scattered due to the skin in contact with the treatment light exit window 16 produces an image of the skin region at the image sensor 30. An exemplary image is shown in FIG. 5(*b*) of the skin on the forearm of a user obtained using the arrangement in FIG. 2. The brighter parts of the image correspond to the air gaps formed by skin creases, skin folds, etc. (which is where the treatment light exit window 16 is in contact with air having refractive index $n_2$), and the darker parts of the image correspond to the parts in contact with skin (which has refractive index $n_3$).

Thus, the arrangement shown in FIG. 2 enables images of the skin region being treated to be obtained, while the light-based treatment operation is being performed, and without risks to the privacy of the user being increased.

Figure 6:
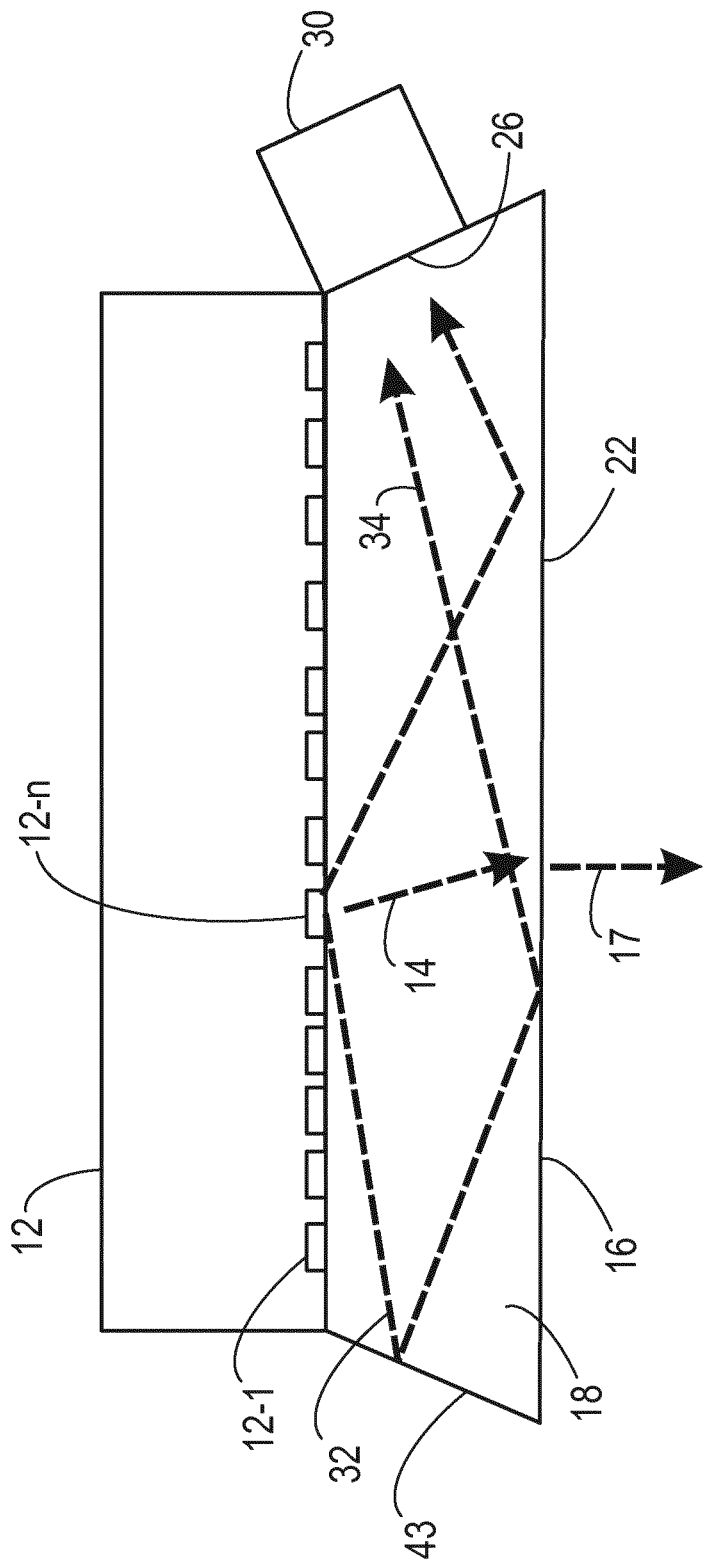
FIG. 6 is a cross-section through an exemplary skin treatment device according to a second embodiment of the invention.

FIG. 6 shows a second embodiment of the skin treatment device 10 according to the invention. The second embodiment is similar to the first embodiment shown in FIG. 2, except that in this embodiment the treatment light source 12 provides the light for generating the image of the skin region, and so no separate imaging light source is required.

It will be appreciated that, unless otherwise indicated below, the features of the second embodiment correspond to those in the first embodiment above. Thus, in this second embodiment the skin treatment device 10 primarily comprises a treatment light source 12, an optical waveguide 18 and an image sensor 30.

In this exemplary embodiment, the treatment light source 12 comprises a plurality of light sources 12-1, . . . , **12-*n*, such as LEDs, that emit treatment light in a broad pattern (i.e. the light is not focussed). As such, the light is emitted from the individual light sources 12-*n* in a number of different directions, as indicated by dashed lines 14, 32, 34**.

In this embodiment, as no separate imaging light source is provided, the optical waveguide 18 is structured or configured such that part of the treatment light from the treatment light source 12 is directed towards the main surface 22 at an angle that leads to total internal reflection of the treatment light at the main surface 22 towards the imaging light exit surface 26 and image sensor 30. Thus, in this embodiment, the optical waveguide 18 comprises a treatment light receiving surface 20, a main surface 22 that is on the opposite side of the optical waveguide 18 to the treatment light receiving surface 20, an imaging light reflecting surface 43 and an imaging light exit surface 26. The imaging light reflecting surface 43 is arranged with respect to the main surface 22 such that it reflects treatment light 32 from at least one of the light sources 12-$n$ towards the main surface 22 below the critical angle $\theta_c$ for the optical waveguide 18 and air (measured with respect to an axis extending perpendicularly from the main surface 22). This treatment light will be totally internally reflected at parts of the main surface 22 where no skin is in contact with the treatment light exit window 16, and frustrated total internal reflection will occur at parts of the main surface 22 where skin is in contact with the treatment light exit window 16.

In some embodiments, the imaging light reflecting surface 43 can be a mirrored (or otherwise reflective) surface such that light incident on the imaging light reflecting surface 43 from within the optical waveguide 18 is reflected by the imaging light reflecting surface 43.

In some embodiments, the optical waveguide 18 can be such that light from the environment is unable to enter the optical waveguide 18 through the imaging light reflecting surface 43. For example the imaging light reflecting surface 43 can be opaque to prevent light in the environment entering the optical waveguide 18. Alternatively, at least the imaging light reflecting surface 43 of the optical waveguide 18 can be contained within the housing of the skin treatment device 10 such that the imaging light reflecting surface 43 is not exposed to the environment.

Figure 7:
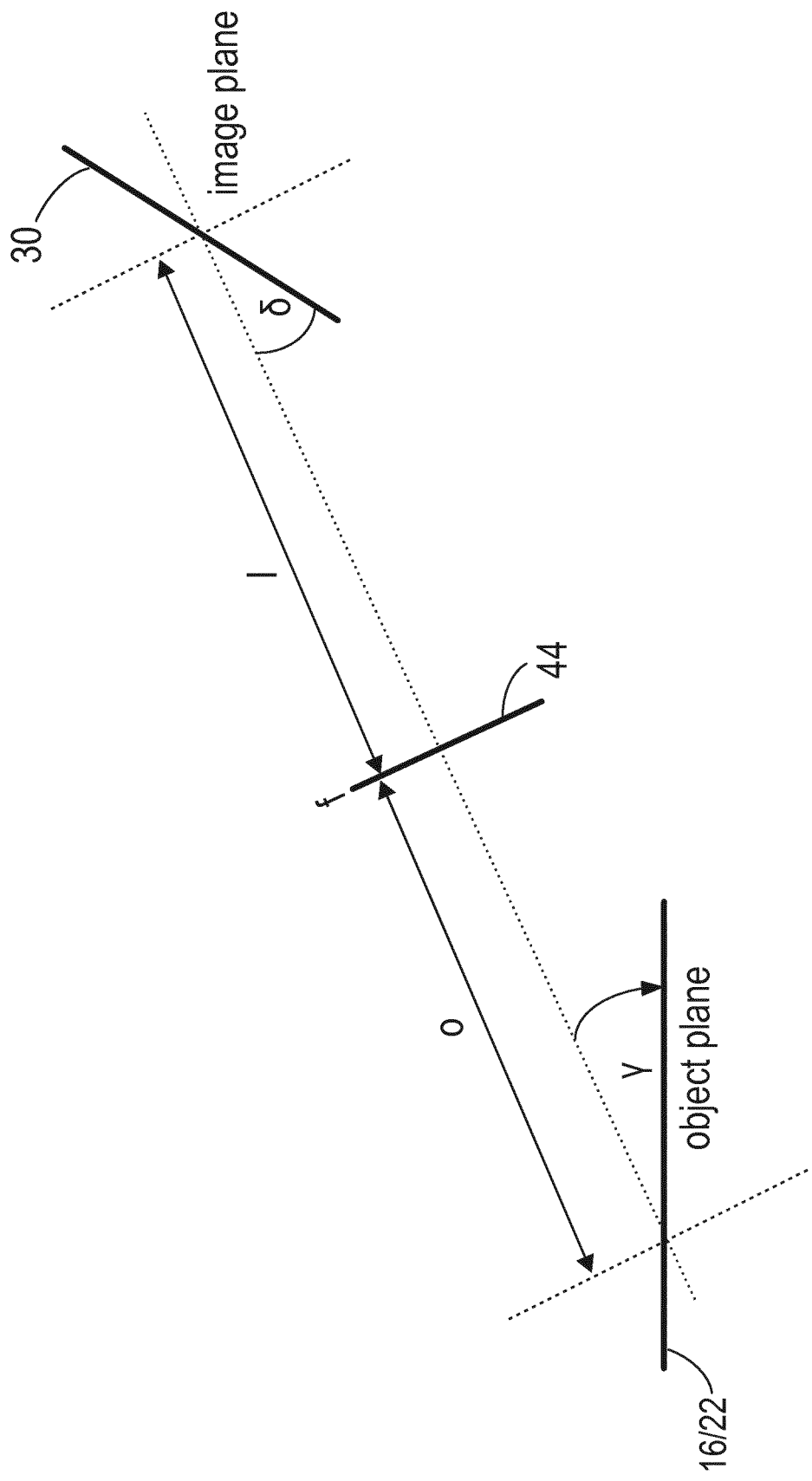
FIG. 7 illustrates the rotation of the plane of the image sensor to reduce distortion in the obtained image.

In either of the embodiments described above (i.e. as shown in FIG. 2 or FIG. 6), it will be appreciated that, if the image sensor 30 is arranged such that the imaging plane (i.e. the plane of the image sensor 30) is perpendicular to the reflected light 34, the image of the skin region generated by the image sensor 30 will be distorted due to the plane of the skin region not being parallel to the plane of the image sensor 30 (this is known as a keystone effect). Thus, in some embodiments the image sensor 30, or more particularly the image plane of the image sensor 30, can be oriented to reduce or avoid this distortion. This orientation is illustrated in FIG. 7. In FIG. 7 the object plane corresponds to the plane of the main surface 22/treatment light exit window 16, and the line 30 represents the image plane of the image sensor 30. An imaging lens 44 is shown that is part of the imaging unit 27 (and in some embodiments can be part of, or integral with, the image sensor 30), that acts to focus the reflected light 34 onto the image sensor 30. In this embodiment the imaging lens 44 has a focal length f, the centre of the object plane is at a distance o from the lens 44 (which is known as the object distance) and the centre of the image plane 30 is at a distance 1 from the lens 44 (known as the image distance). The reflected light 34 (which is parallel to the optical axis) is at an angle $\gamma$ with respect to the object plane/main surface 22 and passes through the lens 44 onto the image sensor 30. The imaging lens 44 provides a vertical magnification denoted Mv.

To reduce or avoid distortion of the image generated of the skin region due to the keystone effect, the image plane 30 is oriented/rotated with respect to the incident reflected light 34 such that the reflected light 34 is incident onto the image plane 30 at an angle $\delta$. The angle $\delta$ is related to the angle $\gamma$ by the following relationship:

$$\tan(\delta)=1/Mv*\tan(\gamma) \qquad (4)$$

In an alternative embodiment to FIG. 7, the image sensor 30 can be arranged so that the imaging plane 30 is perpendicular to the incident reflected light 34, but the imaging lens 44 can be rotated with respect to the light 34 such that the light 34 is incident on the imaging lens 44 at an angle $\delta$. In this embodiment, the rotation of the imaging lens 44 effects the correction of the distortion in the obtained image.

As noted above, in some embodiments the processing unit 36 can process or analyse the images obtained by the image sensor 30. This processing can be used to determine the location of the skin treatment device 10 on the skin of the user, an effect of the skin treatment on the skin region being treated and/or to determine an operating parameter or a change in operating parameter for the light-based treatment operation.

Thus, in some embodiments, the processing unit 36 can process the image or images obtained by the image sensor 30 to determine an effect (or lack thereof) of the light-based treatment on the skin region. The effect of the treatment may depend on the type of treatment being performed, for example hair removal, phototherapy, pain relief, and based on the determined effect, the processing unit 36 can then determine whether to adjust an operating parameter of the treatment operation. For example the processing unit 36 can determine that the intensity of the treatment light should be increased or decreased, the duty cycle (i.e. the flashing on and off of the treatment light by the treatment light source 12) should be changed, or the treatment light should be deactivated, etc. In the case of a treatment light source 12 that comprises an array of LEDs, one or more of the LEDs can be selectively activated or deactivated based on information derived from the image or images. For example, the processing unit 36 may identify that there is a mole in the skin region being treated, and deactivate the LEDs associated with that part of the skin region.

Figure 8:
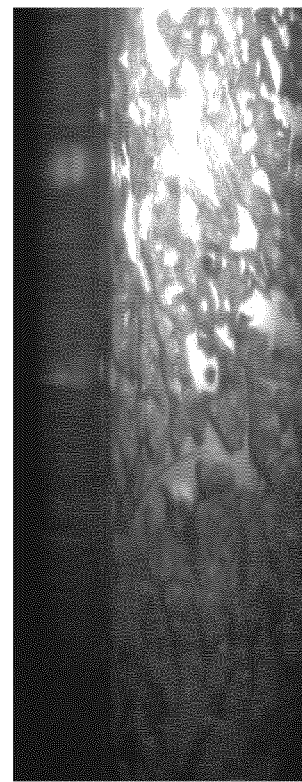
FIG. 8 shows four images obtained by an image sensor when different parts of the skin of a user are in contact with the treatment light exit window.
Figure 8:
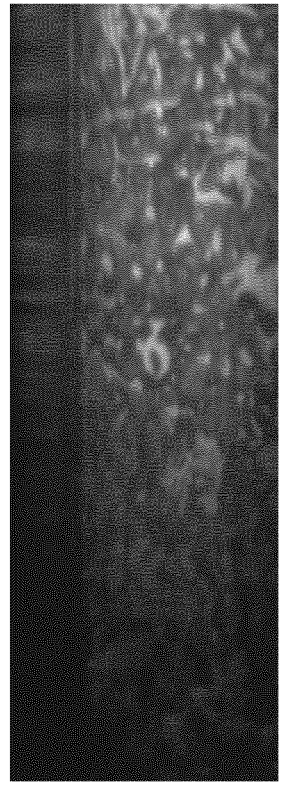
Figure 8:
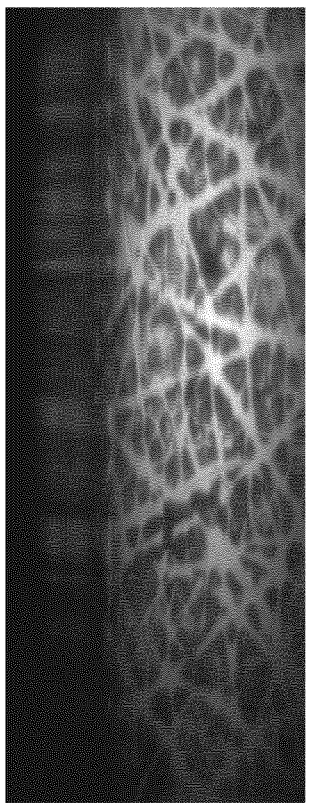
Figure 8:
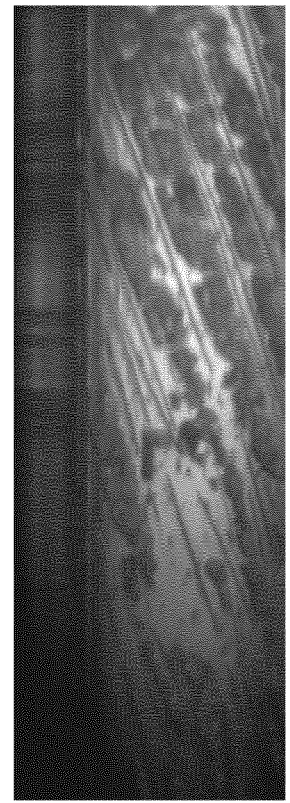

FIG. 8 shows four images obtained by an image sensor 30 when different parts of the body of a user are in contact with the treatment light exit window 16. FIG. 8(a) is an image of skin on the forearm, FIG. 8(b) is an image of skin on the cheek, FIG. 8(c) is an image of skin on the upper lip, and FIG. 8(d) is an image of the skin on the nose. It can be seen that various features of the skin are distinguishable in each image, and the areas of skin in each image differ from each other in structure and composition of those features. In particular, the forearm image (FIG. 8(a)) shows a number of skin folds and hairs, the cheek image (FIG. 8(b)) shows a number of hairs and pores (the white areas where total internal reflection has occurred), the upper lip image (FIG. 8(c)) shows a number of hairs and the nose image (FIG. 8(d)) shows a number of pores. These differences in structure and composition of the skin features can be used to identify the type of skin that is in the obtained image.

Therefore, in some embodiments, the processing unit 36 can be configured to process an obtained image to identify features of the skin and/or hair in contact with the treatment light exit window 16. The processing unit 36 can then determine the location of the treatment light exit window 16 (and thus the skin treatment device 10) on the skin or body of the user based on the identified features. The features can comprise any one or more of contours or surface texture features of the skin, distance between contours or surface texture features of the skin, the colour of the skin, the composition of the skin, the presence of hairs, the density of hairs, the thickness of hairs and the colour of hairs. Those skilled in the art will be aware of various image analysis techniques that can be used to process the obtained image to extract information on these features, and therefore further details are not provided herein.

In some embodiments, the processing unit 36 determines the location of the treatment light exit window 16 and the skin treatment device 10 on the body or skin by comparing the identified features of the skin and/or hair to one or more reference images associated with different locations on the body. The reference images can be stored in a database (e.g. within a memory unit associated with the processing unit 36). For example, the images in FIG. 8 could be reference images for the forearms, cheek, upper lip and nose, and a newly obtained image, or features of the skin and/or hair derived therefrom, could be compared to the reference images (or features of the skin and/or hair derived therefrom) to determine which part of the body the new image has been obtained from. It will be appreciated that there may be a plurality of reference images for each type of skin or each body part to improve the reliability of the classification. The reference image(s) can be obtained from the user themselves, for example in a calibration phase for the skin treatment device 10, and/or they can be based on images obtained from a population of possible users.

In alternative embodiments, the processing unit 36 can determine the location of the treatment light exit window 16 and skin treatment device 10 on the body or skin by comparing the identified features of the skin and/or hair to information on the features of the skin and/or hair for different parts of the body that are stored in a database (e.g. within a memory unit associated with the processing unit 36). The information stored in the database reference image(s) can be obtained from the user themselves, for example in a calibration phase for the skin treatment device 10, and/or they can be obtained from images of different areas of skin for a population of possible users.

In some embodiments, based on the determined location of the skin treatment device 10 on the body or skin, the processing unit 36 can then determine whether to adjust an operating parameter of the treatment operation based on the determined location, or to recommend a particular operating parameter for the user to select on the skin treatment device 10. For example, different types of skin on different parts of the body may require different treatment parameters, and the processing unit 36 can determine and use the appropriate parameters for that part of the body. Thus, for example the intensity of the treatment light could be increased or decreased for the type of skin at the determined location (e.g. skin on the face may require a different wavelength to skin on the arms to avoid side effects, and thick armpit hair may require a higher intensity than thin hair on the legs), the duty cycle (i.e. the flashing on and off of the treatment light by the treatment light source 12) could be changed, or the treatment light could be deactivated if the type of skin should not be subject to the treatment operation, etc.

In some embodiments, the processing unit 36 can monitor the location or locations that the skin treatment device 10 has been used on and provide usage information to the user, for example indicating whether all required areas have been treated, whether any areas have been under-treated or over-treated, etc.

Figure 9:
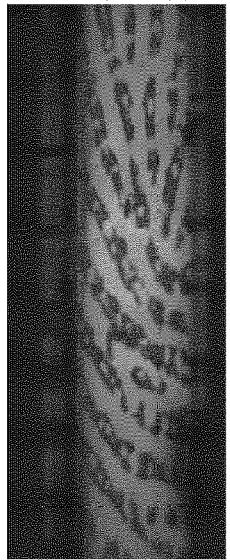
FIG. 9 shows three images obtained of a finger with the treatment light exit window applied to the finger at three different pressures.
Figure 9:
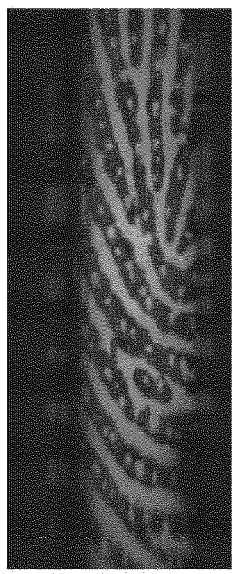
Figure 9:
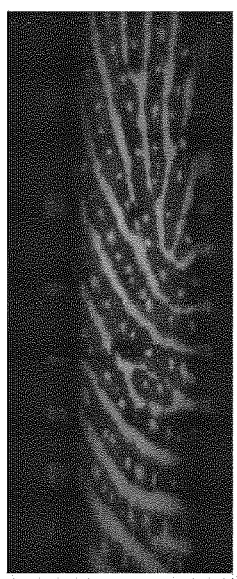

It has been found that the pressure with which the skin treatment device 10 and the treatment light exit window 16 are pressed on to the skin does not significantly prevent the processing unit 36 from determining the location of the skin treatment device 10 on the body or skin. Although the pressure affects the brightness of the obtained image (with higher pressures the amount of skin in direct contact with the treatment light exit window 16 increases and, thus, the amount of frustrated total internal reflection at the treatment light exit window 16 increases), the presence and distance between features, such as creases, skin folds and hairs, remains the same, and the general morphology of the skin remains the same. FIG. 9 shows three images of the skin of a finger with the skin treatment device 10 applied with three different pressures (100 grams (g) in FIG. 9(a), 500 g in FIG. 9(b) and 1000 g in FIG. 9(c)), and it can be seen that the brightness of the images decreases with increasing pressure, but the skin folds are still clearly visible and the spacing therebetween does not change. Thus, even with variations in the application pressure of the skin treatment device 10 onto the skin, it is still possible for the images to be processed to determine the location of the skin treatment device 10 on the body.

In some embodiments, particularly where it is important for the skin treatment device 10 to be applied to the skin with an appropriate amount of pressure, the processing unit 36 can process the received image(s) to estimate the pressure with which the optical waveguide 18 is pressed on to the skin. This pressure can be estimated based on the brightness of part of or all of the obtained image. Alternatively, the processing unit 36 can process the received image(s) to estimate an amount of distortion in the image due to the pressure with which the treatment light exit window 16 is pressed on to the skin (which distorts the optical waveguide 18), and to estimate the pressure with which the treatment light exit window 16 is pressed on to the body based on the estimated distortion. This distortion can be measured by correlating the distance between features (e.g. skin folds, hairs, etc.) and the area in contact with the treatment light exit window 16 (which provide the dark regions of the image). In either of these embodiments, the processing unit 36 can use the estimated pressure to determine feedback for the user of the skin treatment device 10, for example indicating whether the user is pressing the skin treatment device 10 on to the skin at the correct pressure, too hard, or not hard enough. This feedback can be provided to the user by a user interface component on the skin treatment device 10.

In alternative embodiments, rather than estimate the pressure from the obtained image, the skin treatment device 10 can comprise a pressure sensor for measuring the pressure with which the treatment light exit window 16 is pressed onto the skin of the user. The processing unit 36 can be configured to provide feedback for the user of the skin treatment device 10 based on the measurement by the pressure sensor, for example indicating whether the user is pressing the skin treatment device 10 on to the body at the correct pressure, too hard, or not hard enough. Alternatively or in addition, the processing unit 36 can use the measured pressure to determine an amount of distortion present in the obtained image due to the pressure with which the treatment light exit window 16 is being applied to the skin. This distortion can be used to improve the pattern recognition for skin tracking and mapping and skin location identification.

Figure 10:
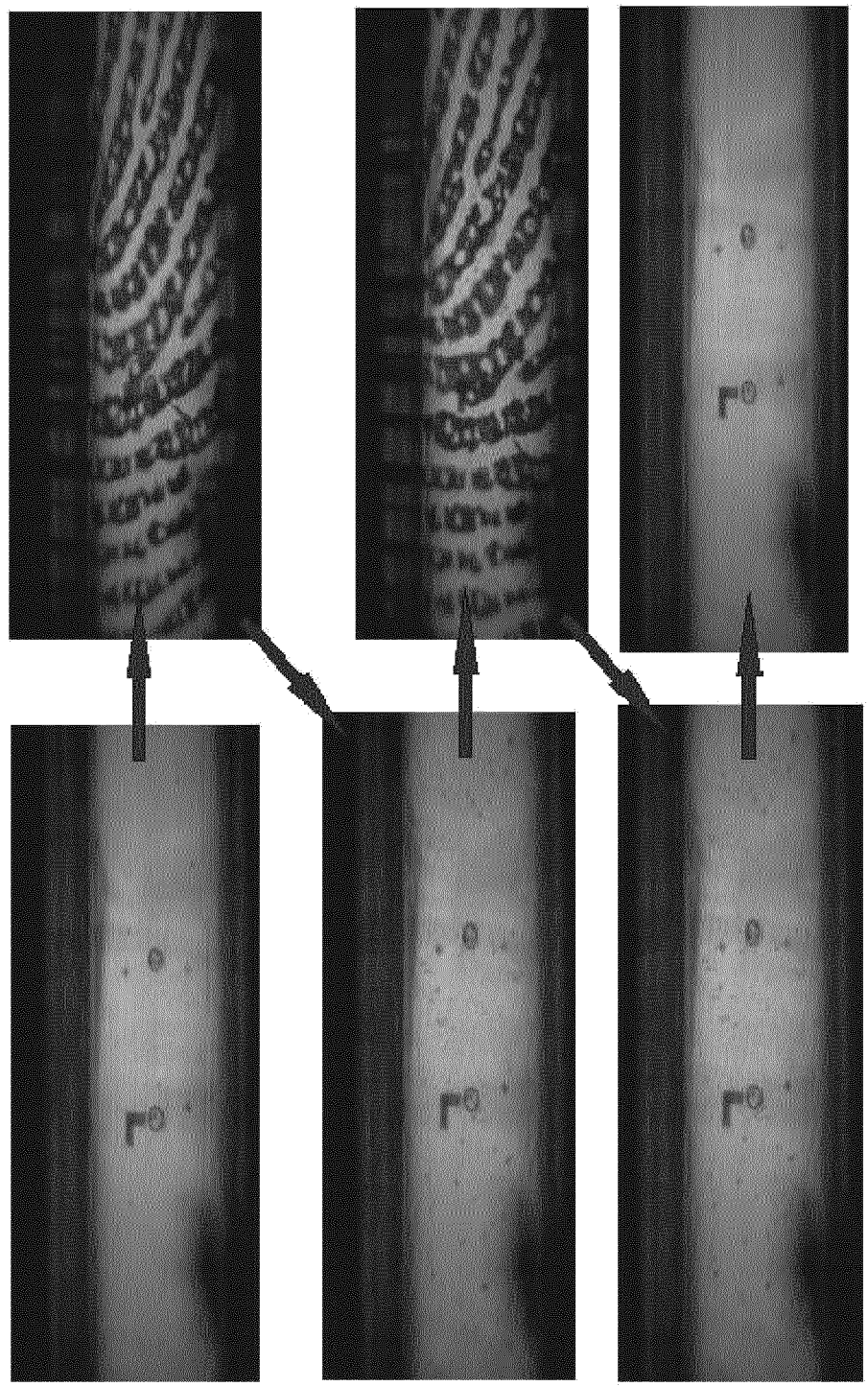
FIG. 10 shows the effect of the cleanliness of the treatment light exit surface on the quality of the obtained images.

It has been found that grease or oils present on the treatment light exit window 16 of the optical waveguide 18, for example those that are naturally present in or on skin, do not significantly affect the quality of the images obtained using the arrangement in FIG. 2. FIG. 10 shows the effect of cleanliness of the treatment light exit window 16 on the obtained images. Thus the first image is obtained when the treatment light exit window 16 is relatively clean. The second image is obtained when a greasy finger is touching the treatment light exit window 16. On removing the finger, some darker spots are visible in the third image caused by the presence of oil/sebum on the treatment light exit window 16 (and frustrated total internal reflection occurring at those points). The fourth image is obtained after placing the finger back onto the treatment light exit window 16, and it can be seen that, despite the oil/sebum on the treatment light exit window 16, the morphological features of the skin are still clearly visible and do not appear to be significantly affected by the presence of the grease. The fifth image shows the oil/sebum after the finger is removed again, and the sixth image shows the effect of wiping the treatment light exit window 16 to remove most of the grease/oil.

In some embodiments, the processing unit 36 can process an obtained image to remove noise from the image due to dirt, grease or other types of contaminants on the treatment light exit window 16. This processing can comprise the steps of using a reference image that was obtained when the treatment light exit window 16 was not in contact with the skin of the user. For example, this processing can comprise the step of removing noise from the fourth image in FIG. 10 using the information in the third image. For example the third image can be considered as a baseline image showing the contaminants (or imperfections) on the treatment light exit window 16, and this can be subtracted from the image obtained when the finger is pressed on the treatment light exit window 16.

In some embodiments, the processing unit 36 can process the obtained image to determine an amount of contaminants on the treatment light exit window 16 of the optical waveguide 18, and to issue an alert to the user if the amount of contaminants is above a threshold amount (for example to prompt the user to clean the treatment light exit window 16). The obtained image can be an image obtained when no skin is in contact with the treatment light exit window 16 (e.g. the third image in FIG. 10), and the amount of contaminants can be determined by comparing the obtained image to a uniformly bright (homogenous) image.

There is therefore provided a skin treatment device that enables images to be obtained of a skin region being treated, while a light-based skin treatment operation is being performed, and that avoids the possibility of the image sensor being able to obtain images of the environment around the user, thereby addressing privacy concerns. The skin treatment device further enables the images of the skin to be obtained in the same position on the skin where the actual treatment is performed or to be performed. In certain embodiments, the obtained image(s) can be used to provide a personalised treatment experience for the user, for example by adjusting the treatment operation based on information in the obtained image(s). In some embodiments, the obtained images can be used to determine the location of the skin treatment device on the body (i.e. the location on the body being treated).

Variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality. A single processor or other unit may fulfil the functions of several items recited in the claims. The mere fact that certain measures are recited in mutually different dependent claims does not indicate that a combination of these measures cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A light-based skin treatment device comprising:
a treatment light source;
a treatment light exit window via which, during operation, treatment light generated by the treatment light source is applied to skin of a user, wherein the treatment light exit window comprises an optically transparent material arranged to contact the skin during operation; and
an imaging unit comprising an image sensor arranged to generate an image of the skin during operation;
an optical waveguide comprising a treatment light receiving surface, an imaging light exit surface and a main surface, wherein:
said treatment light receiving surface is arranged to receive the treatment light so that the treatment light enters the waveguide at the treatment light receiving surface;
said main surface comprises the treatment light exit window and is arranged to transmit the treatment light so that the treatment light exits the waveguide at the treatment light exit window; characterized in that said imaging light exit surface is arranged with respect to the main surface to receive light reflected at the main surface by total internal reflection at positions where, during operation, the image sensor generates the image of the skin where no skin is in contact with the main surface;
said image sensor is arranged to receive from the imaging light exit surface light which is guided by total internal reflection from the main surface towards the imaging light exit surface.

2. The light-based skin treatment device as claimed in claim 1, wherein the image sensor is arranged to generate the image based on parts of the light reflected at the main surface by total internal reflection at positions that are not in contact with skin during operation and attenuated light caused by frustrated total internal reflection of light at positions on the main surface in contact with skin during operation.

3. The light-based skin treatment device as claimed in claim 2, wherein:
the imaging unit further comprises an imaging light source different from the treatment light source;
the optical waveguide further comprises an imaging light receiving surface different from the treatment light receiving surface for receiving imaging light generated by the imaging light source; and
the imaging light receiving surface is arranged with respect to the main surface such that imaging light received by the imaging light receiving surface is incident on the main surface and reflected towards the imaging light exit surface by total internal reflection at positions where, during operation, no skin is in contact with the main surface.

4. The light-based skin treatment device as claimed in claim 3, wherein the imaging light source is arranged with respect to the optical waveguide such that the imaging light is incident on the main surface at an angle less than a critical angle ($_c$) measured with respect to the main surface for the optical waveguide.

5. The light-based skin treatment device as claimed in claim 1, wherein the optical waveguide further comprises:

an imaging light reflecting surface different from the main surface for reflecting at least part of the treatment light received by the treatment light receiving surface towards the main surface such that said reflected part of the treatment light is reflected towards the imaging light exit surface at the main surface by total internal reflection at positions where, during operation, no skin is in contact with the main surface.

6. The light-based skin treatment device as claimed in claim 5, wherein the treatment light source and the imaging light reflecting surface are arranged with respect to the optical waveguide such that said part of the treatment light reflected from the imaging light reflecting surface is incident on the main surface at an angle less than a critical angle ($_c$) measured with respect to the main surface for the optical waveguide.

7. The light-based skin treatment device as claimed in claim 1, further comprising:
 a processing unit that is configured to receive the image from the image sensor and to process the received image.

8. The light-based skin treatment device as claimed in claim 1, wherein the image sensor has a lens arrangement to focus the image sensor at the treatment light exit window.

9. The light-based skin treatment device as claimed in claim 1, wherein the treatment light receiving surface and the main surface are parallel to each other.

10. A light-based skin treatment device as claimed in claim 7, further comprising:
 a treatment light source;
 a treatment light exit window via which, during operation, treatment light generated by the treatment light source is applied to skin of a user, wherein the treatment light exit window comprises an optically transparent material arranged to contact the skin during operation; and
 an imaging unit comprising an image sensor arranged to generate an image of the skin during operation;
 an optical waveguide comprising a treatment light receiving surface, an imaging light exit surface and a main surface, wherein:
 said treatment light receiving surface is arranged to receive the treatment light so that the treatment light enters the waveguide at the treatment light receiving surface;
 said main surface comprises the treatment light exit window and is arranged to transmit the treatment light so that the treatment light exits the waveguide at the treatment light exit window; characterized in that said imaging light exit surface is arranged with respect to the main surface to receive light reflected at the main surface by total internal reflection at positions where, during operation, no skin is in contact with the main surface;
 said image sensor is arranged to receive from the imaging light exit surface light which is guided by total internal reflection from the main surface towards the imaging light exit surface;
 a processing unit that is configured to receive the image from the image sensor and to process the received image;
 a pressure sensor for measuring a pressure with which the treatment light exit window is pressed onto the skin of the user;
 wherein the processing unit is configured to process the measured pressure to determine an amount of distortion present in the received image due to the pressure.

11. The light-based skin treatment device as claimed in claim 10, wherein the processing unit is configured to process the received image to determine a location of the light-based skin treatment device on the skin of the user, determine an effect of the treatment light on the skin being treated, and/or determine an operating parameter or a change in operating parameter for the treatment light source.

12. The light-based skin treatment device as claimed in claim 11, wherein the processing unit is configured to process the received image to identify features of the skin in contact with the treatment light exit window, and to determine the location of the light-based skin treatment device on the skin of the user based on the identified features of the skin.

13. The light-based skin treatment device as claimed in claim 11, wherein the processing unit is configured to process the received image to identify features of the skin in contact with the treatment light exit window, and to determine the location of the light-based skin treatment device on the skin of the user by comparing the identified features of the skin to one or more reference images associated with different locations on the skin.

14. The light-based skin treatment device as claimed in claim 11, wherein the processing unit is configured to process the received image to identify features of the skin in contact with the treatment light exit window, and to determine the location of the light-based skin treatment device on the skin by comparing the identified features of the skin to information on the features of the skin for different parts of the skin that is stored in a database.

15. A light-based skin treatment device comprising:
 a treatment light source;
 a treatment light exit window via which, during operation, treatment light generated by the treatment light source is applied to skin of a user, wherein the treatment light exit window comprises an optically transparent material arranged to contact the skin during operation; and
 an imaging unit comprising an image sensor arranged to generate an image of the skin during operation;
 an optical waveguide comprising a treatment light receiving surface, an imaging light exit surface and a main surface, wherein:
 said treatment light receiving surface is arranged to receive the treatment light so that the treatment light enters the waveguide at the treatment light receiving surface;
 said main surface comprises the treatment light exit window and is arranged to transmit the treatment light so that the treatment light exits the waveguide at the treatment light exit window; characterized in that said imaging light exit surface is arranged with respect to the main surface to receive light reflected at the main surface by total internal reflection at positions where, during operation, no skin is in contact with the main surface;
 said image sensor is arranged to receive from the imaging light exit surface light which is guided by total internal reflection from the main surface towards the imaging light exit surface;
 a processing unit that is configured to receive the image from the image sensor and to process the received image;
 a pressure sensor for measuring a pressure with which the treatment light exit window is pressed onto the skin of the user, wherein the processing unit is configured to process the measured pressure to determine an amount of distortion present in the received image due to the pressure;

wherein the processing unit is further configured to process the received image to estimate an amount of distortion in the image due to a pressure with which the treatment light exit window is pressed on to the skin of the user, and to estimate the pressure with which the treatment light exit window is pressed on to the skin of the user based on the estimated distortion.

16. The light-based skin treatment device as claimed in claim 15 wherein the processing unit is further configured to process the received image to compensate for noise in the image due to contaminants on the treatment light exit window.

17. The light-based skin treatment device as claimed in claim 15 wherein the processing unit is further configured to process the received image to determine an amount of contaminants on the treatment light exit window, and to issue an alert to the user if the amount of contaminants is above a threshold amount.

18. The light-based skin treatment device as claimed in claim 15, wherein the image sensor is arranged to generate the image based on parts of the light reflected at the main surface by total internal reflection at positions that are not in contact with skin during operation and attenuated light caused by frustrated total internal reflection of light at positions on the main surface in contact with skin during operation.

19. The light-based skin treatment device as claimed in claim 15, wherein the optical waveguide further comprises:

an imaging light reflecting surface different from the main surface for reflecting at least part of the treatment light received by the treatment light receiving surface towards the main surface such that said reflected part of the treatment light is reflected towards the imaging light exit surface at the main surface by total internal reflection at positions where, during operation, no skin is in contact with the main surface.

20. The light-based skin treatment device as claimed in claim 19, wherein the treatment light source and the imaging light reflecting surface are arranged with respect to the optical waveguide such that said part of the treatment light reflected from the imaging light reflecting surface is incident on the main surface at an angle less than a critical angle ($\theta_c$) measured with respect to the main surface for the optical waveguide.

* * * * *